(12) United States Patent
Morozov

(10) Patent No.: US 7,918,980 B2
(45) Date of Patent: Apr. 5, 2011

(54) ELECTROCAPTURING FLOW CELL

(75) Inventor: Victor Morozov, Manassas, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 1308 days.

(21) Appl. No.: 11/397,906

(22) Filed: Apr. 5, 2006

(65) Prior Publication Data

US 2006/0260942 A1   Nov. 23, 2006

Related U.S. Application Data

(60) Provisional application No. 60/668,061, filed on Apr. 5, 2005.

(51) Int. Cl.
*G01N 27/453* (2006.01)

(52) U.S. Cl. ......... 204/518; 204/542; 204/627; 204/628

(58) Field of Classification Search .......... 204/518–542, 204/627–640
See application file for complete search history.

(56) References Cited

U.S. PATENT DOCUMENTS

| | | | | | |
|---|---|---|---|---|---|
| 4,661,224 | A | * | 4/1987 | Goldstein et al. | 204/522 |
| 5,942,443 | A | * | 8/1999 | Parce et al. | 506/39 |
| 2002/0023842 | A1 | * | 2/2002 | Ogle | 204/627 |
| 2003/0127333 | A1 | * | 7/2003 | Lauks et al. | 204/600 |

* cited by examiner

*Primary Examiner* — Arun S Phasge
(74) *Attorney, Agent, or Firm* — Edgar Rodriguez; David G. Grossman

(57) ABSTRACT

A flow cell for electrophoretically-assisted capturing analytes from a flow. The flow cell includes a specimen chamber, a first membrane, a second membrane, a first electrode chamber, and a second electrode chamber. The specimen chamber may have a sample inlet and a sample outlet. A first portion of the first membrane may be coupled to a first portion of the specimen chamber. A first portion of the second membrane may be coupled to a second portion of the specimen chamber. The first electrode chamber may be configured to accept a charge. A portion of the first electrode chamber may be coupled to a second portion of the first membrane. A second electrode chamber may be configured to accept an opposite charge. A portion of the second electrode chamber may be coupled to a second portion of the second membrane.

21 Claims, 9 Drawing Sheets

US 7,918,980 B2

ELECTROCAPTURING FLOW CELL

CROSS-REFERENCES TO RELATED APPLICATIONS

This application claims priority of U.S. Provisional Patent Application Ser. No. 60/668,061, filed Apr. 5, 2005, which is hereby incorporated by reference.

STATEMENT REGARDING FEDERALLY FUNDED SPONSORED RESEARCH OR DEVELOPMENT

The U.S. Government has a paid-up license in this invention and the right in limited circumstances to require the patent owner to license others on reasonable terms as provided for by the terms of Grant No. DE-F C52-04NA25455 awarded by the Department of Energy.

BRIEF DESCRIPTION OF THE DRAWINGS

The following drawings describe some embodiments of the present invention.

DETAILED DESCRIPTION OF EMBODIMENTS

Embodiments will now be described in detail with reference to the accompanying drawings. It should be understood that the embodiments and the accompanying drawings have been described for illustrative purposes and the present invention is limited only by the claims. Further, those skilled in the art will appreciate that various modifications, additions and substitutions are allowed without departing from the scope and spirit of the invention as set forth in the accompanying claims.

An embodiment of a flow cell for electrophoretically-assisted capturing analytes from a flow cell includes a specimen chamber, a first membrane, a second membrane, a first electrode chamber, and a second electrode chamber. The specimen chamber may have a sample inlet and a sample outlet. A first portion of the first membrane may be coupled to a first portion of the specimen chamber. A first portion of the second membrane may be coupled to a second portion of the specimen chamber. The first electrode chamber may be configured to accept a charge. A portion of the first electrode chamber may be coupled to a second portion of the first membrane. A second electrode chamber may be configured to accept an opposite charge. A portion of the second electrode chamber may be coupled to a second portion of the second membrane.

This and other embodiment described in this disclosure use external forces to bring analytes to a surface loaded with probe molecules capable of capturing and keeping the particles immobilized. The analytes may be part of the active assay. Analytes may include viruses and other pathogens. Application of external forces should not significantly change conditions such as temperature and composition of solution. In particular, the embodiments for electrophoretically assisted capturing from flow (further referred to as an electrocapturing flow cell) may exchange heat produced in the electrophoretic electrocapturing to allow an application of high voltage. To avoid changes in composition of solutions due to electrochemical reaction on electrodes the electrodes may be remotely placed or the solution around the electrodes may be quickly exchanged. Therefore embodiments should enable the active capturing of analytes from a flow of a liquid sample onto a functionalized surface membrane.

Figure 1:
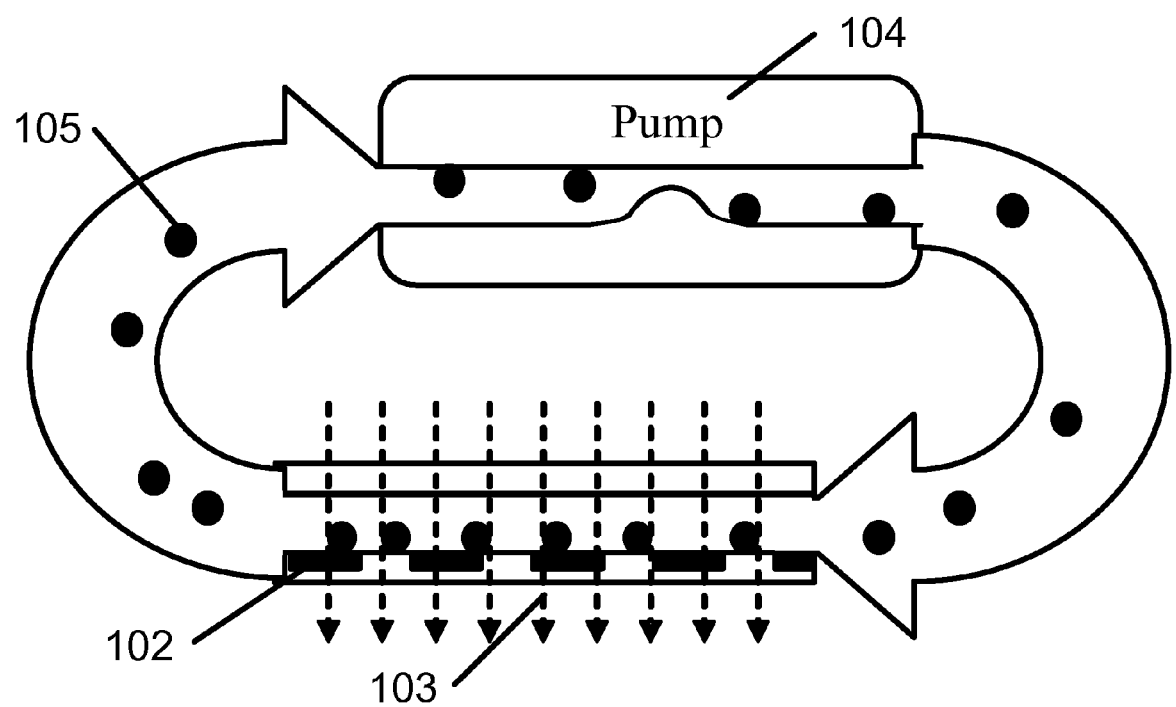
FIG. 1 is a general schematic describing electrocapturing from flow according to an aspect of an embodiment of the present invention.

FIG. 1 is a general schematic illustrating analytes 105 being captured on an array surface 102 from a pump flow in the presence of a normal force 103 applied to analyte molecules or units 105. Analytes 105 may be circulated through a closed circulatory system by a pump 104. During each pass, analytes 105 may bond to probe molecules on the array surface 102. Those analytes 105 which missed the probe molecules 102 in one run may be returned by the pump 104 to the same array multiple times. The recirculation process is intended to facilitate the capture of most or all of the analytes 105. Upon recycling the analyte solution, analytes 105 may track the surface until they are bound. Applying a normal force 103 may increase the speed and efficiency of detecting and binding analytes 105 by removing a gap between analytes 105 in a solution and the array surface while the analytes 105 are dragged or rolled along the array surface with the flow of the solution. The analytes 105 probe for a multitude of locations on the array surface for the presence of a specific binder.

Examples of forces that may be employed to press the analytes 105 against the array surface include electric, centrifugal and magnetic forces.

Figure 2:
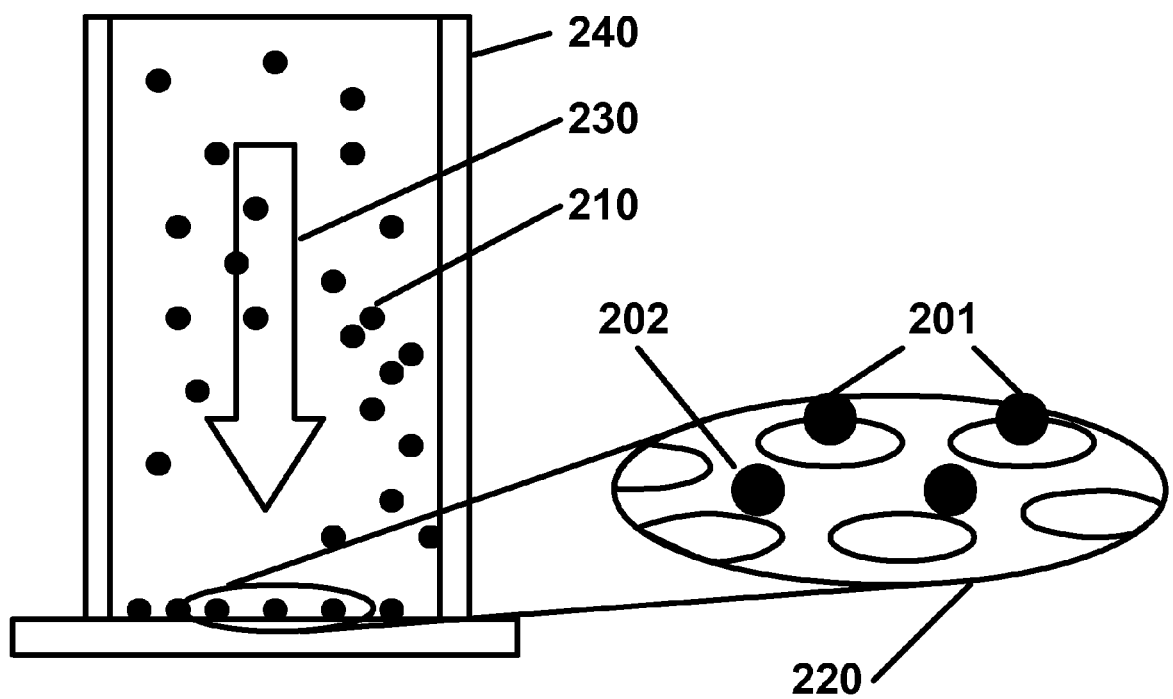
FIG. 2 is an exploded perspective view showing capture of analytes from an immobile solution or suspension.

FIG. 2 shows captured analytes 201 and lost analytes 202 in the presence of a normal force 230 but in the absence of a lateral flow. Normal electric force 230 may be applied to analytes 210 to direct them down to an array 220 at the bottom of electrophoretic cell 240. Pathogens or other analytes 210, which happen to land between the probe molecule spots or onto spots coated with non-specific antibodies, probably will not bind to the array and may be lost upon subsequent washing. Thus, FIG. 2 shows a technique that should capture analytes 210 proportionally to the fraction of array 220 surface occupied by specific antibodies.

Figure 3:
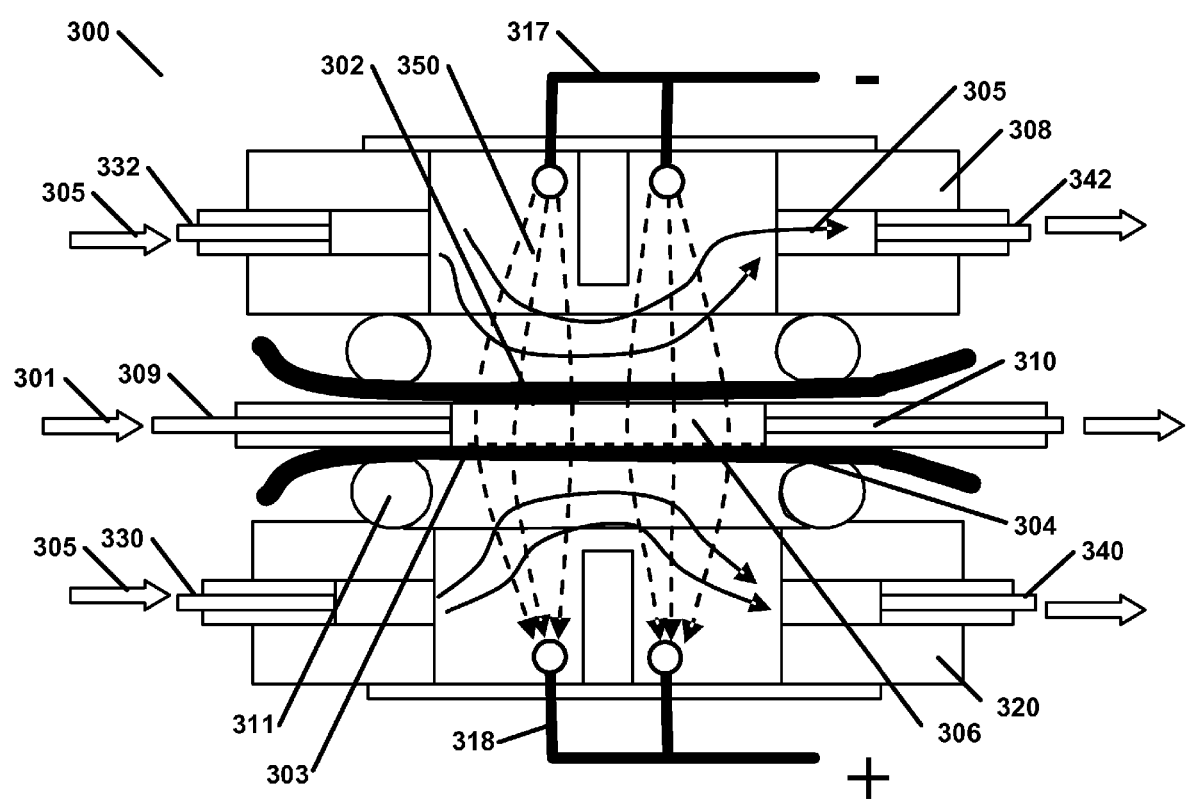
FIG. 3 is a cross sectional view of a flow cell according to an aspect of an embodiment of the present invention.

FIG. 3 shows an embodiment of an electrocapturing flow cell that includes three main elements. The three elements include a specimen chamber 306, a first electrode chamber 308, and, second electrode chamber 320. The first electrode chamber 308 may be coupled to a first side of specimen chamber 306. The second electrode chamber 320 may be coupled to a second side of specimen chamber 306.

Analyte solution 301 can enter the specimen chamber 306 through specimen chamber inlet 309. Analyte solution 301 may flow in a narrow gap between the two membranes 302 and 303. The lower membrane 303 may bear an array 304 of probe molecules that have an affinity for analytes or markers attached to analytes. Analytes and markers attached to analytes may include antibodies, DNA, RNA, oligonucleotides, and lectins.

The outer sides of membranes 302 and 303 may face flow of buffer solution 305 in the upper electrode chambers 308 and lower electrode chambers 320 respectively. Heat generated in the specimen chamber 306 may be dissipated by providing a narrow gap for the buffer solution 305 to flow through. An electric force 350 may be selectively increased or decreased by adjusting the electrode-membrane distance. For example, Electrodes 317 and 318 may be placed close to membrane surfaces 302 and 303 respectively to achieve a relatively strong electric field 350 and placed farther away from the membrane surfaces 302 and 303 to achieve a relatively weaker electric field 350. Products of the electrode reaction may be washed away from the membrane surfaces 302 and 303 with a flow of buffer solution 305.

Buffer solution 305 may flow through the two electrode chambers 308 and 320 respectively. The electrode chambers 308 and 320 include electrodes 317 and 318 respectively. Electrodes 317 and 318 should be constructed of conductive materials such as platinum wire or the like. The electrode chambers 308 and 320 may be made of a transparent material to allow visual control of flow 305 as well as microscopic control and monitoring of binding events in the flow cell 300. The electrode chambers 308 and 320 and the specimen chamber 306 may be kept together while in the working state using numerous methods. For example, the connection of the electrocapturing flow cell 300 may include the use of one or more of the following elements: elastic O-rings, screws, vacuum, and glue.

Theoretical analysis may be made to estimate how quickly an analyte solution 301 may be pumped through an embodiments of an electrocapturing flow cell to enable a high capture rate of analytes such as viruses, while limiting temperature arise inside the cell by a certain value, $\Delta T$. For example, volume rate may be described by the following formula: $V \sim bL_\chi h^{-1} (\lambda \Delta T/\sigma)^{1/2}$. Here, b and L are the width and the length (along the flow) of the capturing cell; h is the gap between two membranes; $\chi$ is the analyte mobility; $\lambda$ is the heat conductance of the buffer solution; $\Delta T$ is a tolerable increase in the temperature within the capturing cell, and $\sigma$ is the electrical conductivity of buffer. It may be seen from the formula, that two major factors that could be used to increase capturing rate are (i) decreasing the gap between the membranes and (ii) decreasing electric conductivity of samples. Although capturing surface area, bL, may be increased, this may result in a proportional decrease of the surface density of the bound analytes, which may not be desirable.

Working through an illustrative example, one could use an adenovirus with $\chi=2\times10-4$ cm$^2$/Vs. Assuming that $\Delta T=5°$ C., and taking the real parameters of the first prototype: L=5 mm, b=3.5 mm, h=1 mm, $\lambda=0.6$ Wt/m grad (water) and $\sigma=0.1$ Sm$^{-1}$ (corresponds to 10 mM NaCl solution) one can see from the formula that V~0.1 mL/min, with the maximum electric field E=55 V/cm, the total current of 10 mA and a power of W=0.05 Wt.

As follows from the equation, to achieve an efficient collection of biological particles within a given area of the capturing membrane, one may need to have very thin gap, h, between the membranes.

Figure 4:
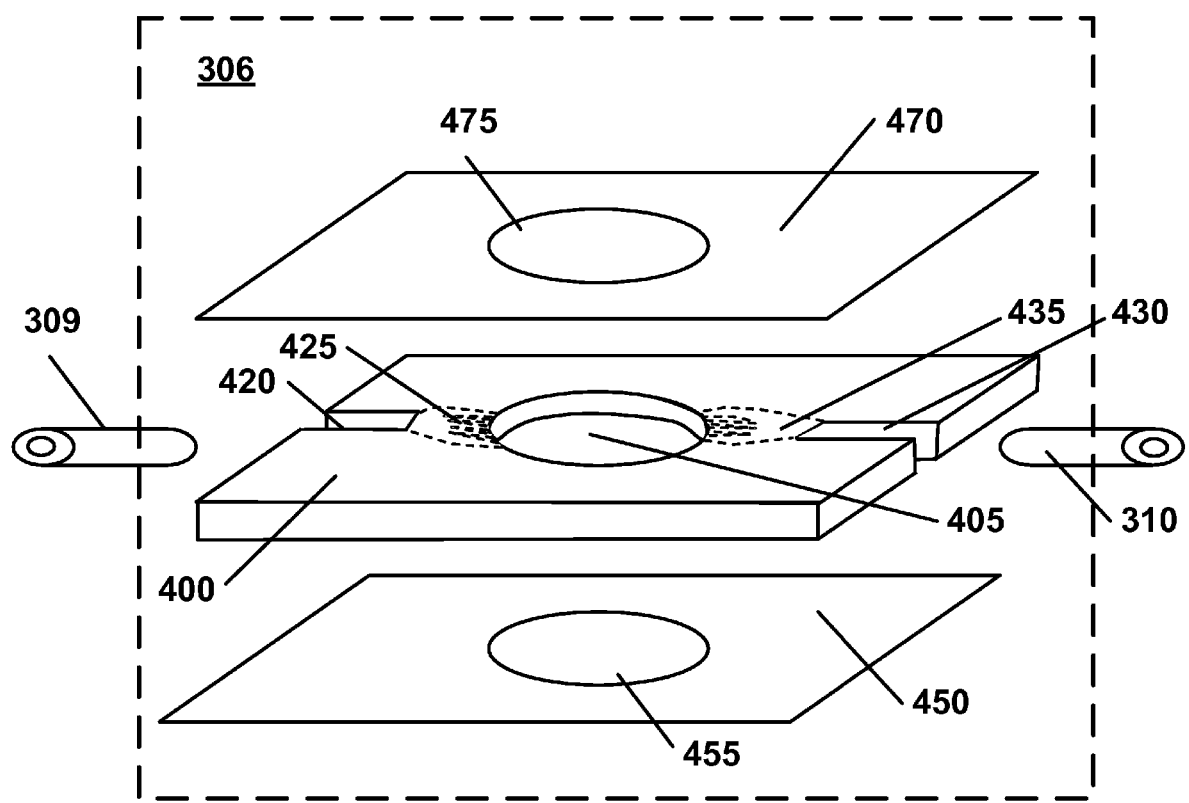
FIG. 4 is an exploded perspective view of an alternative embodiment of element 306 shown in FIG. 3.
Figure 5:
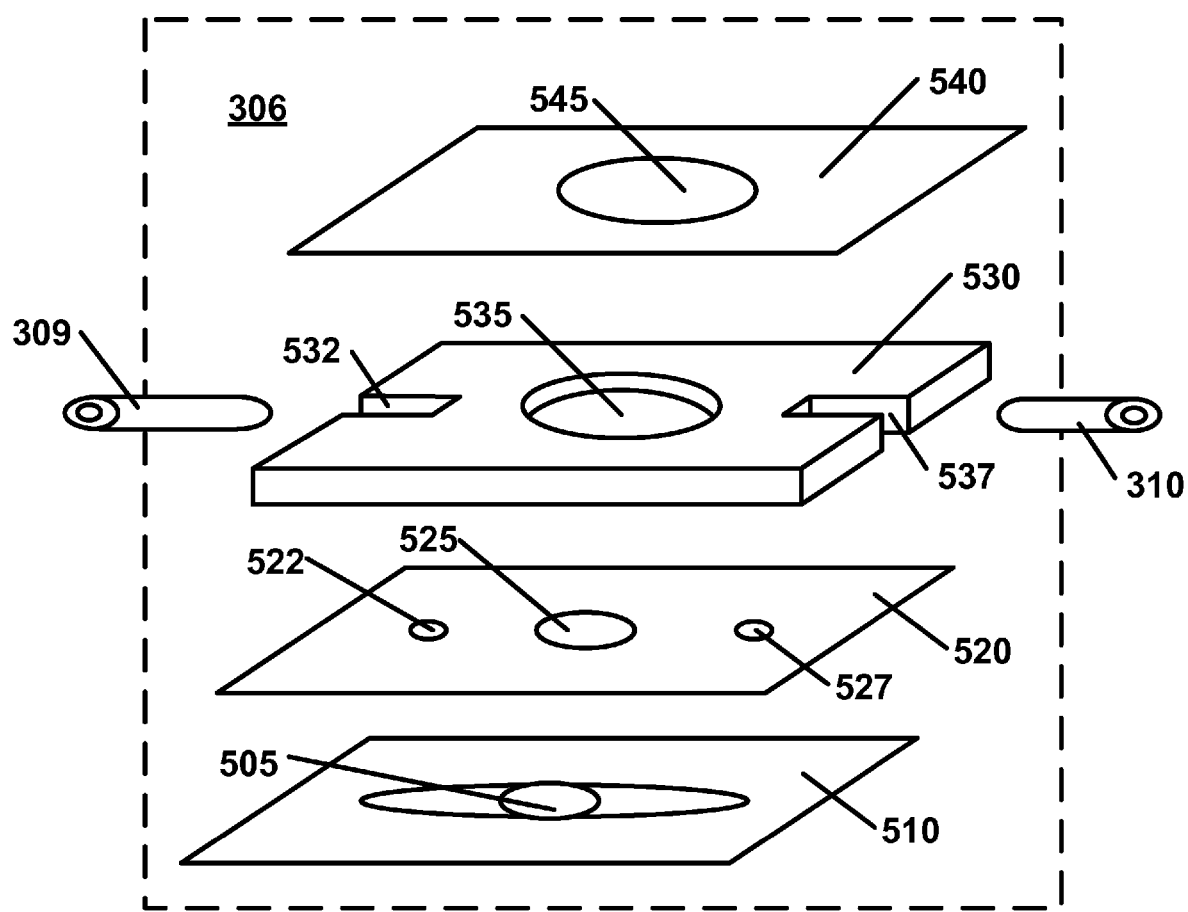
FIG. 5 is an exploded perspective view of an second alternate embodiment of element 306 shown in FIG. 3.

Two embodiments of the specimen chamber 306 used as an integral part of the electrophoretic flow cell 300 are presented schematically in FIGS. 4 and 5. It may be helpful for some parts of the flow cell to be transparent such as all or part of electrode chambers 308 and 320. Transparent materials that may be used include glass, fused quartz, plastic, or other comparable transparent material.

In the embodiment shown in FIG. 4 the specimen chamber 306 includes three plates: plate 400, plate 470, and plate 450. Plate 400 which may be thicker than plates 470 and 450, has a central opening 405 and an inlet groove 420 for receiving inlet tube 309 and groove 430 for receiving outlet tube 310. A series of channels 425 may be engraved on the upper surface of plate 400 between inlet groove 420 and central opening 405. Similarly, a series of channels 435 may be engraved on the upper surface of plate 400 between central opening 405 and outlet groove 430. In at least one embodiment the microchannels may be engraved 50-100 micrometers deep. However one skilled in the art will recognize that the depth and width of the channels may vary to optimize the flow and capture of analytes in the analyte solution. These grooves 425 and 435 may be made by micromachining, by etching or other available techniques. Plate 470 may have a central opening 475 and plate 450 may have a central opening 455. These central openings 455 and 475 may be substantially identical to the opening 405 in plate 400 by size and shape. All three plates 400, 450 and 470 may be connected together by numerous ways including elastic O-rings, screws, vacuum, or glue. Inlet tube 309 and outlet tube 310 may be adapted to the grooves 420, 430 respectively. Analyte solution 301 may be fed through inlet tube 309, through groove 420 and the series of microchannel 425 to reach the central opening 405. Preferably, the diameter of the inlet tube 309 and outlet tube 310 should not exceed the thickness of the central plate 400.

The embodiment shown in FIG. 4 may also be constructed using a microscopic slide for central plate 400 and cover slips for plates 470 and 450. A typical gap when using microscopic slides and cover slips may be approximately 1.3 mm thick. The openings and grooves 425 and 435 may be etched with an acid such as hydrofluoric acid. Microscope slides and cover slips may be obtained from Cole-Parmer of Vernon Hills, Ill. and DR Instruments of Palos Hills, Ill.

FIG. 5 is an exploded perspective view of a second alternate embodiment of element 306 shown in FIG. 3. This embodiment illustrates yet another way in which the gap in the specimen chamber 306 may be reduced. In this embodiment, the gap may be made of plates 510 and 520. Plate 510 has a central opening 505 and plate 520 may have a central opening 525. Two small openings 522 and 527 may be made in plate 520 to allow analyte solution 301 to penetrate between plates 510 and 520. Before connecting plates 510 and 520, a sacrificial strip (not illustrated) of material may be placed between the plates 510 and 520. The plates 510 and 520 may be connected using a glue that polymerizes without changing its volume such as epoxy or photo-activated glue. After the plates 510 and 520 are connected, the sacrificial strip may be removed to expose a gap in the space between the two plates 510 and 520. The removal of the sacrificial strip may be easier if the sacrificial strip is relatively flexible. The just created gap should now connect the central openings 525 and 505 with the small openings 522 and 527.

An alternative way to create a gap without using a sacrificial strip is to etch grooves in one or both plates 510 and 520 before joining. To further connect the inlet tube 309 and outlet tube 310 tubes and to reinforce the specimen chamber 306 in general, a plate 530 may be attached to the top of the connected plates 510 and 520. Plate 530 may be thicker than the joined plates 510 and 520, however, one skilled in the art will recognize that a properly attached lamination may provide reinforcement even if plate 530 is not thicker than connected plates 510 and 520. The grooves may be cut in the plate 530 so that their ends reach the position of small openings 522 and 527 in plate 520. A central opening 535 with a diameter that may be larger than the size of the central openings 525 and 505 in plates 510 and 520 respectively, may be fabricated in the plate 530. These openings may be fabricated using a drill.

A third plate 540 with a large central opening 545 and two tubes (not illustrated) may be attached to plate 530. In this embodiment, the gap may constitute the thickness of the two thin plates 510, 520 and an adhesive layer. As noted earlier, the size of the gap may be adapted to various properties such as the viscosity of the analyte solution, the dimensions of the plates, the strength of the electric field and the anticipated flow rate.

To avoid flipping the membrane, pressure in the electrode chambers 308 and 320 should be kept identical to the pressure in the specimen chamber 306. One way to keep the pressures equal may be to include pressure sensors into the electrode chambers 308 and 320 that communicate to feedback control element(s) that control the pumps feeding the electrode chambers 308 and 320 as well as the specimen chamber 306. Yet another way to keep the pressures equal consists of making inlets 309, 330 and 332 of substantially smaller diameter than outlets 310, 340, and 342, which should keep the pressure inside the electrode chambers 308 and 320 and specimen chamber 306 relatively low.

Figure 6:
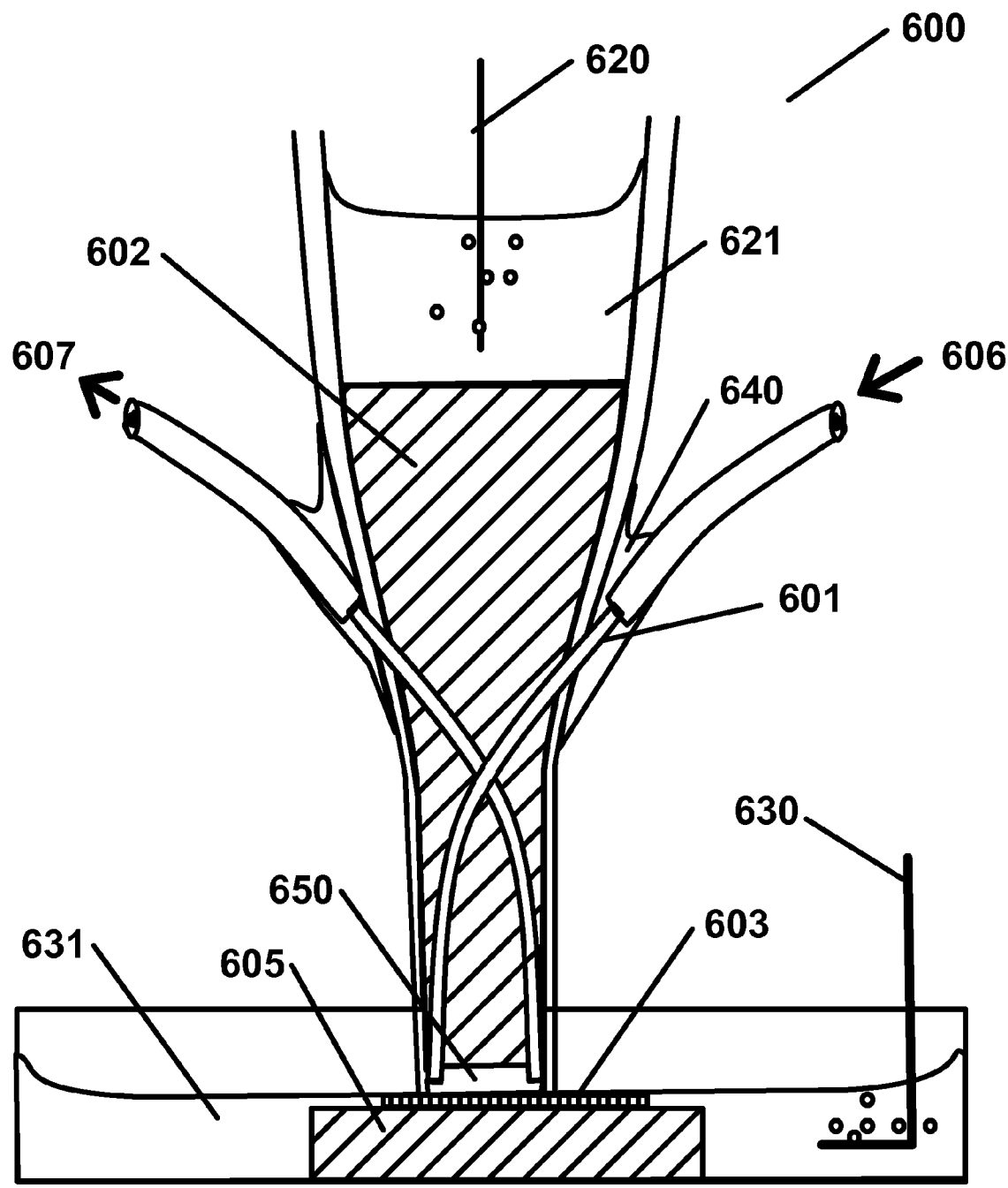
FIG. 6 is a schematic diagram of an aspect of an embodiment of the present invention which uses an agarose.

In yet another embodiment, shown in FIG. 6, the upper membrane 602 in a electrocapturing flow cell 600 includes a hydrogel layer 602 such as agarose or polyacrylamaide gel. The hydrogel membrane layer 602 may be configured to function as an ion-permeable wall of the specimen chamber 650. A microarray 603 may be deposited on a lower membrane 605 making a wall of the specimen chamber 650. The lower membrane 605 may be a hydrogel slab configured to keep the flow cell tight while allowing flow of electric current through electrodes 620 and 630. This hydrogel slab 605 may be a thick agarose gel slab. Electrode 620 may be located in electrolyte solutions 621 which touches a portion of the hydrogel membrane layer 602. Similarly, electrode 630 may be located in electrolyte solutions 631 which touches a portion of the lower membrane 605. The inlet analyte solution 301 may be pumped through the flow cell via inlet tube 606 and outlet tube 607 embedded in the agarose gel 602. The inlet tube 606 and outlet tube 607 may be held in place through a mechanical stabilizing mechanism 640 such as epoxy. Inlet tube 606 and outlet tube 607 may be microcapillary tubes.

Figure 7:
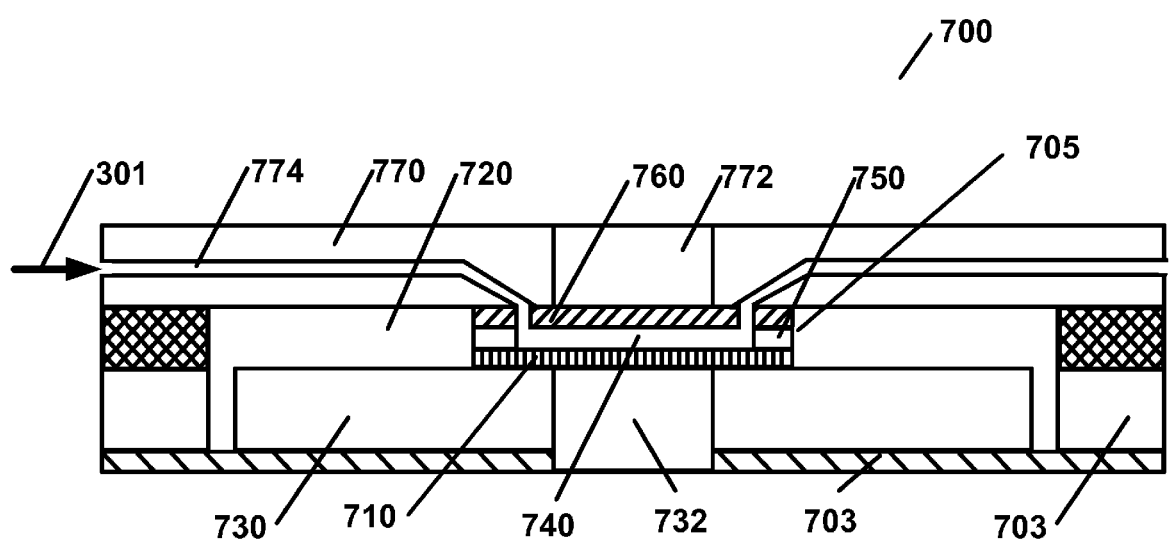
FIG. 7 is a sectional view of an embodiment of the present invention where some elements of the electrocapturing flow cell may be held together using a pressure differential.

A further embodiment of an electrophoretic cell 700 is illustrated in FIG. 7. A microarray 710 may be pressed against an opening 732 in a lower plate 730 so that its active surface is exposed to a flow specimen chamber 740 formed by spacer(s) 750 and membrane 760 attached to the upper cover 770. Plates 730 and 770 may be made of a transparent material. Membrane 760 may be attached by glue to cover 770. The cover 770 may contain an opening 772 and a system for feeding capillaries 774, enabling a flow of analyte solution 301. The cover 770 and plate 730 may be held together by external air pressure when pressure in space 720 between plates 730 and 770 is lower than the external pressure. One way to lower the pressure is to use a vacuum pump. Another way to create such a pressure differential would to be assemble the flow cell 700 in an lower pressure environment and then move the flow cell 700 into a higher pressure environment for use. Such clamping may allow relatively rapid assembly and disassembly of the flow cell 700. This may be valuable if the flow cell 700 is used with automated devices. Openings 732 and 772 in the electrophoretic cell 700 may be filled with electrolyte and connected to electrodes. A support (not illustrated) may hold the flow cell and provide contact with electrolyte chambers.

Some experimental results will now be described as examples to help illustrate how the different embodiments operate. A first experiment captures MS2 phages from a flow 301 using an embodiment of a capturing device 300 similar to the one illustrated in FIGS. 3 and 4.

Figure 8:
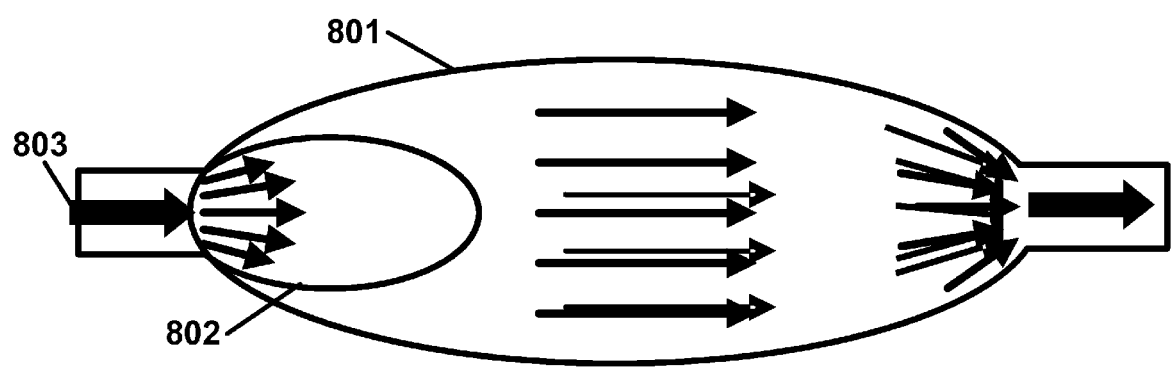
FIG. 8 is a schematic view showing a distribution of captured analytes in the active area of a binding membrane.

The electrophoretic capturing device 300 was used to capture MS-2 bacteriophages from 1 mL of solution. The phage stock solution was diluted 1:250 with 10 mM MES buffer, pH=6.7. Capturing was performed at the rate of 40 µL/min with the voltage of 150 V and a current of 1 mA. Polyethyleneimine (PEI) coated dextran layer, on a dialysis membrane was used to capture negatively charged phages on the positively charged PEI-surface. After 1 mL of the phage solution passed the electrocapturing flow cell the membrane was rinsed with water, glued to a glass support and subjected to Atomic Force Microscopy (AFM) imaging. It was found that MS2 phages were observed only at the part of the total membrane area 801 exposed to the electric field. This area 802 was close to the entrance of the flow cell 803 and has the shape outlined in the FIG. 8. Area 802 was 1 mm high and 2 mm across.

One may conclude from such a distribution, that (i) the solution was completely depleted from the phages after it passed 2 mm distance in the active capturing area 603 and that (ii) all the phage particles present in the sample were collected in the limited area indicated. Taking the average surface density of MS2 particles in images, $4\pm1$ $\mu m^{-2}$, and the surface of the elliptic spot, $S=(\frac{1}{4})\pi$ ab=1.6 mm$^2$, one can estimate the total number of phages in 1 mL as $N=4\times1.6\times10^6=6.4\times10^6$ particles, which gave $1.6\times10^9$ phages/mL of the stock solution, close to $(2-3)\times10^9$ phages/mL estimated in the independent experiment.

In a second experiment, adenoviruses were electro-captured with anti-adenovirus antibodies arrayed on activated surface of a dialysis membrane. The microarray was fabricated by electrospray deposition of polyclonal antibodies (prepared in goat, obtained from Chemicon International., cat # 1056) through a mesh mask on a dialysis membrane coated with a layer of cross-linked oxidized dextran. The array was blocked with the blocking solution (1% BSA solution in 20 mM TRIS/HCl, pH=7.5, 0.15 NaCl, 0.1% Tween-20).

A stock solution of the adenoviruses was diluted with 10 mM MES buffer, pH=6.5, 0.5% Tween-20 and 1 mL of this solution was passed through the cell 300, 50 µL/min. 100 V was applied to Pt electrodes with the current of 3 mA. After all the volume passed through the cell the array was washed and subjected to two kinds of tests.

In one test, beads functionalized with the same antibodies were pressed against the array surface with a magnet and then another magnet was used to remove weakly bound beads from the surface. As in the case of MS2 capturing described in the first example, it was found that the beads bind only a part of the array area close to the entrance of the flow cell. This part of the cell was then used in the second test in the device for scanning with magnetic beads. The array was placed in the flow cell 300. The cell 300 was placed onto a table of an optical microscope equipped with a dark-field illuminator. A stack of rare earth permanent magnets was placed under the array on top of the illuminator. The flow cell 300 was filled with a suspension of functionalized beads, which were prepared by reaction of biotinilated anti-adenovirus antibodies with commercial super-paramagnetic beads coated with streptavidin. The suspension was allowed to flow through the cell 300 by applying small hydrostatic pressure.

Figure 9:
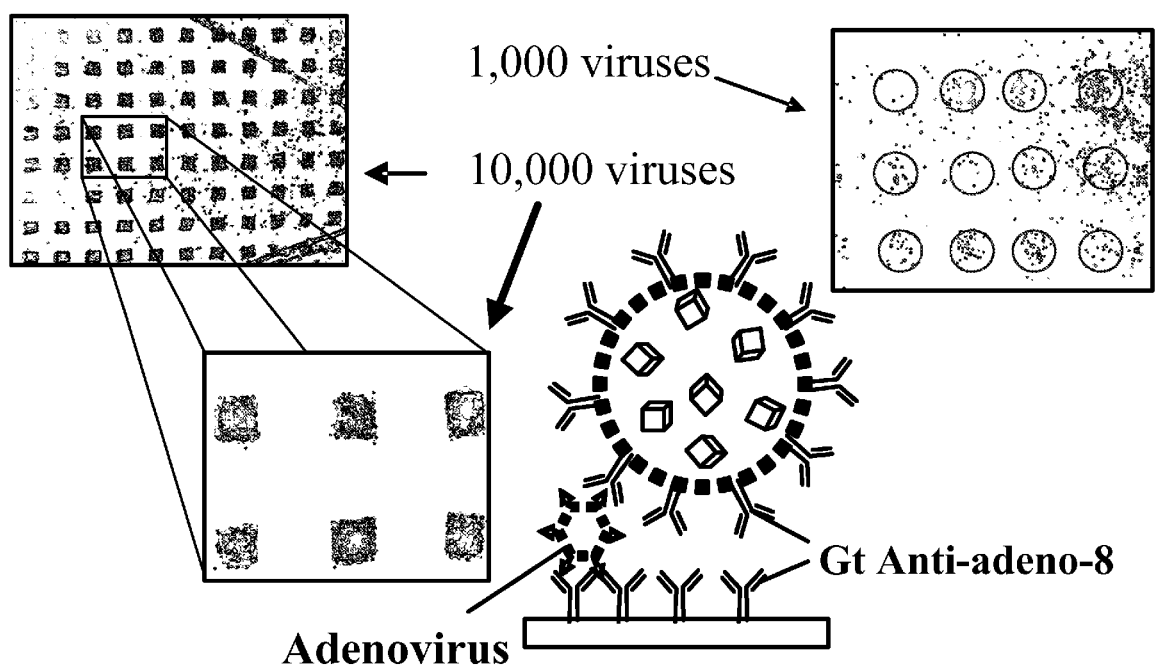
FIG. 9 is a diagram showing the capture of analytes from a suspension using an electrocapturing flow cell according to an embodiment of the present invention

As illustrated in FIG. 9, very distinctive array of beads was seen under dark filed illumination when only 10,000 viruses were present in 1 mL of solution. Even when this number was reduced to 1,000, an array of beads was still observed, albeit it became less bright.

This experiment indicated that viruses could be effectively collected from diluted solutions using an embodiment of the flow electrocapturing and then detected by functionalized magnetic beads or other means.

While various embodiments of the present invention have been described above, it should be understood that they have been presented by way of example, and not limitation. It will be apparent to persons skilled in the relevant art(s) that various changes in form and detail can be made therein without departing from the spirit and scope of the present invention. In fact, after reading the above description, it will be apparent to one skilled in the relevant art(s) how to implement the invention in alternative embodiments. Thus, the present invention should not be limited by any of the above described exemplary embodiments. In particular, it should be noted that, for example purposes, the above explanation has focused the use of plates for structural support. However, those experienced in the art will realize that multiple other embodiments may also provide structural support not just for the electrocapturing flow cell itself, but internal components such as the flexible membranes. For example, structural support for one or both of the membranes may include providing a rigid mesh between the electrode chambers and the specimen chamber.

In addition, it should be understood that any figures, screen shots, tables, examples, etc. which highlight the functionality and advantages of the present invention, are presented for example purposes only. The architecture of the present invention is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope of the present invention in any way.

Furthermore, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A flow cell comprising:
    a specimen chamber, the specimen chamber having:
        a sample inlet; and
        a sample outlet;
    a first membrane, a first portion of the first membrane coupled to a first portion of the specimen chamber;
    a second membrane, a first portion of the second membrane coupled to a second portion of the specimen chamber;
    a first chamber configured to accept a charge, a portion of the first chamber coupled to a second portion of the first membrane; and
    a second chamber configured to accept an opposite charge, a portion of the second chamber coupled to a second portion of the second membrane,
    wherein at least a part of the first portion of at least one of the first membrane and the second membrane is configured to bind an analyte from fluid flow in the specimen chamber under electric force, and is visible from outside the specimen chamber through a transparent portion.

2. A flow cell according to claim 1, wherein at least one of the first membrane and second membrane is one of the following:
    a microfiltration membrane;
    an ion-exchanging membrane.

3. A flow cell according to claim 1, wherein at least one of the first membrane and second membrane includes a hydrogel layer.

4. A flow cell according to claim 1, further including a microarray disposed on either the first membrane or the second membrane.

5. A flow cell according to claim 4, wherein the microarray is composed of binding molecules.

6. A flow cell according to claim 1, wherein microcapillary tubes are coupled to the sample inlet and sample outlet.

7. A flow cell according to claim 1, wherein the sample inlet and sample outlet are coupled to tubes.

8. A flow cell according to claim 1, further including a structural plate coupled between the first membrane and the first chamber.

9. A flow cell according to claim 1, further including a structural plate coupled between the second membrane and the second chamber.

10. A flow cell according to claim 1, wherein the first chamber is configured to accept a flow of buffer solution.

11. A flow cell according to claim 1, wherein the specimen chamber is configured to accept a flow of analyte solution.

12. A flow cell according to claim 1, wherein the pressure difference between the chambers and the specimen chamber is kept sufficiently close to zero.

13. A flow cell according to claim 1, wherein the part of at least one of the first membrane and second membrane is coated with a specific binding reagent that binds to an analyte.

14. A flow cell according to claim 1, wherein the part of at least one of the first membrane and second membrane is coated with a number of binding reagents distributed over the membrane area to form a plurality of binding areas.

15. A flow cell according to claim 1, wherein a distal end of the sample inlet is coupled to the specimen chamber through a plurality of microchannels.

16. A flow cell according to claim 1, wherein a proximal end of the sample outlet is coupled to the specimen chamber through a plurality of microchannels.

17. A flow cell according to claim 1, wherein at least one of the first chamber and the second chamber comprises the transparent portion.

18. A flow cell according to claim 1, wherein a first electrode is disposed within the first chamber and a second electrode is disposed within the second chamber.

19. A flow cell according to claim 17, wherein the transparent portion is a side of at least one of the first and the second chamber.

20. A method for electro-capturing analytes from a flow comprising:
    pumping an analyte solution:
        into a specimen chamber through a sample inlet;
        over a microarray on at least a part of a second portion of at least one of a first membrane and a second membrane configured to bind an analyte from fluid flow in the specimen chamber under electric force; and
        out of the specimen chamber through a sample outlet;
    applying an electric charge to a first electrode, the first electrode disposed in a first electrode chamber; a portion of the first electrode chamber coupled to a first portion of a first membrane, the second portion of the first membrane coupled to a first portion of the specimen chamber;

applying an opposite electric charge to a second electrode, the second electrode disposed in a second electrode chamber; a portion of the second electrode chamber coupled to a first portion of a second membrane, the second portion of the second membrane coupled to a second portion of the specimen chamber, wherein at least the part of the second portion of at least one of the first membrane and the second membrane is visible from outside the specimen chamber through a transparent portion.

21. A method according to claim 19, further including:

pumping a buffer solution through the first electrode chamber; and pumping a buffer solution through the second electrode chamber.

\* \* \* \* \*